United States Patent [19]

Melleney et al.

[11] Patent Number: 4,988,206
[45] Date of Patent: Jan. 29, 1991

[54] METHODS ARE APPARATUS FOR MONITORING THE DIFFUSE REFLECTIVITY OF A SURFACE

[75] Inventors: Derek A. Melleney, Wiltshire; David C. Reeves; Michael Potter, both of Hampshire, all of England

[73] Assignee: De La Rue Systems Limited, London, England

[21] Appl. No.: 165,196
[22] PCT Filed: Jul. 6, 1987
[86] PCT No.: PCT/GB87/00474
    § 371 Date: Apr. 26, 1988
    § 102(e) Date: Apr. 26, 1988
[87] PCT Pub. No.: WO88/00338
    PCT Pub. Date: Jan. 14, 1988

[30] Foreign Application Priority Data
    Jul. 4, 1986 [GB] United Kingdom ............... 8616334

[51] Int. Cl.⁵ ............................................. G01N 21/47
[52] U.S. Cl. ...................................................... 356/446
[58] Field of Search ........................................ 356/446

[56] References Cited

U.S. PATENT DOCUMENTS

| | | | |
|---|---|---|---|
| 3,526,777 | 9/1970 | Robinson et al. | 250/237 |
| 3,718,399 | 2/1973 | Kalman | 356/446 |
| 3,984,189 | 10/1976 | Seki et al. | 356/446 X |
| 4,092,068 | 5/1978 | Lucas et al. | 356/446 X |
| 4,189,235 | 2/1980 | Guter et al. | 356/239 |
| 4,568,191 | 2/1986 | Barry | 356/446 |
| 4,616,933 | 10/1986 | Leveque et al. | 356/445 X |
| 4,666,309 | 5/1987 | Barry et al. | 356/446 |
| 4,823,169 | 4/1989 | Ogura | 356/446 |

FOREIGN PATENT DOCUMENTS

| | | |
|---|---|---|
| 0209860 | 1/1987 | European Pat. Off. |
| 56-148041 | 11/1981 | Japan . |
| 60-149948 | 8/1985 | Japan . |
| 1053386 | 12/1966 | United Kingdom . |

Primary Examiner—Vincent P. McGraw
Attorney, Agent, or Firm—Sughrue, Mion, Zinn, Macpeak & Seas

[57] ABSTRACT

A method and apparatus for monitoring the diffuse reflectivity of a portion of a surface. The method is particularly applicable to soil detection of banknotes. The method comprises exposing the surface portion (3) to a beam of radiation from a source (2). At least one part of the diffuse radiation reflected by the surface portion (3) is sensed by a sensor (6) located closely behind an aperture (7) such that the aperture (7) defines, in effect, a sensing position situated such that the intensity of the diffusely reflected radiation sensed is substantially invariant within a working range of distances (D) between the aperture (7) and the surface portion (3). A value representative of the diffuse reflectivity of the surface portion (3) is then determined from the sensed intensities.

17 Claims, 5 Drawing Sheets

METHODS ARE APPARATUS FOR MONITORING THE DIFFUSE REFLECTIVITY OF A SURFACE

The invention relates to methods and apparatus for monitoring the diffuse reflectivity of a surface which, in the field of banknote handling, can provide a measure of the degree of soiling of banknotes.

There is a well known requirement for the automated sorting of used banknotes based on the amount of dirt or contamination, otherwise known as soiling, which has built up on the notes. Notes deemed to be sufficiently clean are re-issued and the remainder are withdrawn from circulation. Methods which are used to reliably transport used banknotes are not normally compatible with restraining the plane of the banknote within better than about ±2 mm from its nominal position while still allowing a clear view of its surface. The note itself may have fold lines and crinkles which locally remove its surface from the nominal position.

It is important that any means of measurement should be able to make comparative measurements which are significantly more precise and repeatable than may be judged by the un-trained human eye, otherwise notes that are too soiled will be re-issued and notes that are too clean will be withdrawn.

Previous attempts at measuring the soil state of banknotes have either accepted the large inaccuracy in measurement resulting from the uncertainty in the position of the plane of the note, or have used a long optical path between the note and the sensor, such that variations in the length of this path by a few mm do not produce a significant variation in the measured reflectivity. These long optical path length solutions imply large dimensions for the system, or a complex optical system to fold the optical path back on itself many times within small dimensions Long optical path systems also suffer from an intrinsic lack of efficiency in collecting the reflected light, thereby requiring the use of high intensity illumination with the attendant problems of space and heat dissipation requirements.

There are several other constraints on a system intended to measure the soil level of banknotes.

1. The system must have a resolution sufficiently high to enable measurements to be made on unprinted or very lightly printed areas of the note. This is because the human observer naturally makes a judgement on the basis of these unprinted areas, and also because an attempt to make measurements on areas containing significant printing would be significantly influenced by normal variations in the density of the inks.

2. The system should not be sensitive to light specularly reflected from the surface of the banknote. This is because specular reflection is highly angular dependent and would be greatly affected by any tilt in the plane of the banknote, and also because any shiny adhesive tape which may have been used to repair the note would have the effect of making the note appear cleaner than it really is.

An example of a known monitoring system is described in GB-A-No. 2117897 in which a pair of sensors detect diffuse radiation reflected from a surface. This system is designed to look for discontinuities in the surface such as creases and requires a complex detection system to operate successfully. Another example of a known monitoring system is described in US-A-No. 4,092,068 which is concerned with obtaining an indication of topographical surface characteristics such as roughness. In neither example is account taken of the practical problem of movement of the sheet towards or away from the sensing assembly. This is a real problem particularly in the case of high speed sheet feeding apparatus.

In accordance with one aspect of the present invention, a method of monitoring the diffuse reflectivity of a portion of a surface comprises exposing the surface portion to a beam of radiation; sensing the intensity of a part of the diffuse radiation, reflected by the surface portion, at a sensing position situated such that the intensity of the diffusely reflected radiation sensed at the sensing position is substantially invariant within a working range of distances between the sensing position and the surface portion; and determining from the sensed intensity a value representative of the diffuse reflectivity of the surface portion.

In accordance with a second aspect of the present invention, apparatus for monitoring the diffuse reflectivity of a surface comprises a radiation beam source; a surface support member mounted such that the radiation impinges, in use, on a surface supported by the support member; and a radiation sensor for generating a signal for feeding to processing means; the signal corresponding to the intensity of a part of the diffuse radiation reflected by the surface and passing through a sensing position, and the sensing position being situated such that the intensity of the diffusely reflected radiation sensed at the sensing position is substantially invariant within a working range of distances between the sensing position and the surface.

We have investigated in some detail the way in which a surface reflects an incident radiation beam and have found that, at least in a plane containing the incident radiation beam, there is a substantially symmetrical distribution in intensity of the diffusely reflected radiation, and the specularly reflected radiation is reflected through a relatively small range of angles.

By irradiating the surface with a narrow-angle incident beam of radiation, it is ensured that the specular reflection is substantially confined to a narrow angular range. The diffuse reflection sensor, which detects radiation at angles outside the latter angular range, is therefore relatively insensitive to specular reflection.

It has been found, and will be discussed in more detail hereinafter, that the amount of the diffusely reflected radiation passing through a sensing position is proportional to the Lambertian distribution of the reflected radiation, the inverse square law and the area of the sensing position normal to the incident radiation. Calculation reduces these factors to a dependence on the perpendicular or working distance between the sensing position and the surface under examination, the displacement of the sensing position perpendicularly from the beam of radiation before diffuse reflection by the surface under examination, and the angle of inclination or orientation of the sensing position relatively to the surface under examination. In a consideration of the inter-dependence of these three variables, again as will be discussed in more detail hereinafter, it is found that there is relatively little change in the amount of the diffusely reflected radiation passing through a sensing position on either side of a maximum value over a relatively wide range of working distances between the sensing position and the surface under examination. Thus, carefully situating the sensing position compensates for the variations in the working distance which commonly occur particularly when the surface is provided by a sheet which is moving past the apparatus. By following the present invention it is possible to ensure that the sensitivity goes through a peak at the chosen working distance, and changes only slowly each side of this peak. Moreover, the nominal WOrking distance between the sensing position and the surface under examination can be much smaller than has been the case in the past.

A radiation sensor could be placed directly at the sensing position. Preferably, however, an apertured mask is placed between a radiation sensor and the surface portion such that an aperture in the apertured mask is situated at the sensing position. This gives substantially the same result, provided that all of the radiation reaching the aperture is collected by the radiation sensor, but has certain practical advantages. For example, it is often advantageous to introduce a window and/or filter in the mask aperture in front of the radiation sensor. Moreover, radiation sensors are not readily available in a wide range of dimensions. It is therefore more convenient to manufacture an apertured mask to the precise dimensions required, and use this in conjunction with a readily available radiation sensor of standard size.

It would be possible to monitor diffuse reflectivity at just a single sensing position. Preferably, however, the intensity of the diffuse radiation is sensed at two sensing positions, each of the sensing positions being situated such that the intensity of the diffusely reflected radiation sensed at the sensing position is substantially invariant within a working range of distances between the sensing position and the surface portion, and the sensed intensities are averaged to reduce sensitivity to variations in the angular inclination of the surface portion. Such variations can arise if the surface, particularly of a sheet, has folds or crinkles which have the effect of changing the angle of incidence of the irradiating beam on the surface. It has been found by considering the distribution of intensity of the diffusely reflected radiation that this change in angle of incidence simply rotates the symmetrical region. This has the effect that at one sensing position the incident intensity will increase while at the other it will decrease. The average, however, will stay substantially the same and at the value previously obtained with a flat surface.

This leads to high resolution combined with high efficiency and low power consumption within a confined space and avoids the need for the prior art arrangements which required long path lengths.

Although sensors at the two sensing positions could have different responses, which could be compensated for by the processing means prior to generating the intensity values, preferably each sensor has substantially the same sensitivity since this will simplify the processing steps.

Although the two sensing positions could be arranged symmetrically, the two sensing positions are preferably arranged asymmetrically relatively to the surface portion under examination to reduce sensitivity to variations within an extended working range of distances, between the two sensing positions and the surface under examination.

The radiation may comprise white light but other forms of radiation such as infra-red or ultra-violet will also be used where appropriate.

Preferably, the light which reaches the radiation sensor or sensors is filtered to match the response of the system to that of the human eye.

Typically, the apparatus will include a housing to which the radiation beam source and the sensors are mounted. This enables the apparatus to be formed as a compact head allowing precise orientations of the sensors and masks, where appropriate, to be achieved during manufacture. Separate mounting of the components is, however, also possible.

It is important in monitoring systems of this type to ensure that the radiation beam is at a substantially constant intensity or that the detected intensities are modified to compensate for variations in the irradiating beam intensity.

One method which has been commonly used in the past is to sample the irradiating beam before it impinges on a surface and to monitor the intensity of the sampled portion. However, this system does not take into account the problem of build up of dust on the surface of the sensors themselves, as the process of transporting banknotes or the like inevitably produces large quantities of dust. In the past, to deal with this, the sensors have been positioned sufficiently far from the sheet position to allow cleaning.

Preferably, therefore, the method further comprises, causing a reference surface to be exposed to the beam of radiation, sensing diffuse radiation reflected by the reference surface at the or each of the sensing positions to generate respective reference values, and subsequently normalising the intensities sensed at the or each of the sensing positions by comparison with the respective reference values.

For example, at least that part of the support member which is illuminated when no surface is supported may have a substantially uniform reflectance whereby radiation received at the or each of the sensing positions after reflection by said uniform reflectance part is used to set a reference.

Where the methods and apparatus are used in conjunction with monitoring the surfaces of sheets, such as banknotes, fed past the apparatus, it is particularly advantageous to provide the support member with a uniform reflectance portion since the passage of sheets across the support member tends to clean the support member thus maintaining its uniform reflectance.

Typically, the sensors will comprise photosensitive detectors, such as photodiodes or phototransistors.

In order that the invention may be better understood, an example of a preferred embodiment of a banknote soil detector according to the invention will now be described with reference to the accompanying drawings, in which.

Figure 1:
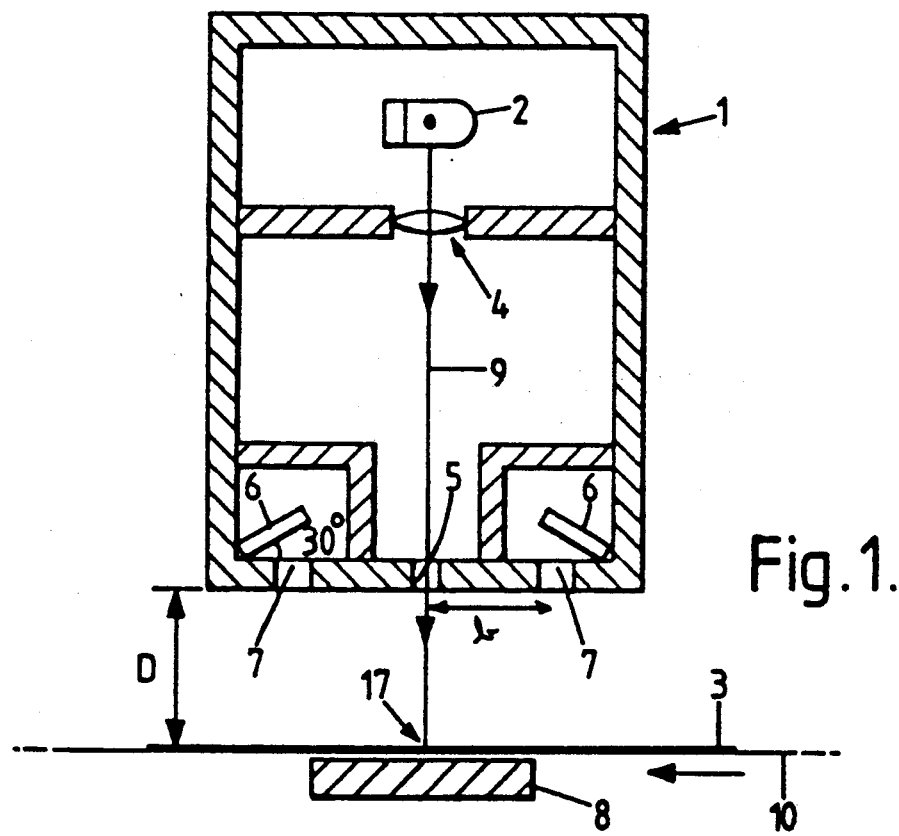
FIG. 1 is a longitudinal section through the detector.
Figure 2:
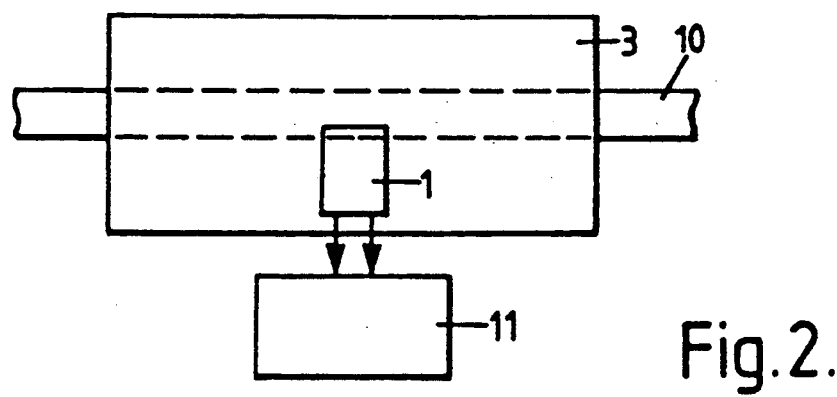
FIG. 2 is a plan showing the detector connected to a microprocessor.

The soil detector shown in FIGS. 1 and 2 comprises a head having a light proof housing 1 inside which is mounted an incandescent bulb 2. A beam 9 defining an image of the filament of the bulb 2 is focussed onto a banknote 3 by means of a converging lens 4 and via a plain glass window 5. Since the light beam 9 impinges substantially normally on the banknote 3, it will be specularly reflected back towards the Window 5. Proportions of the diffuse reflected light will, however, be received by two photodiodes 6, positioned behind two filter glass windows 7 whose centres are at a distance "b" apart from beam 9 thus forming a masked arrangement. The photodiodes 6 are angled towards each other so as to receive radiation from substantially the same portion 17 of the banknote 3. The filter glass is chosen so as to match the spectral response of the system to that of the human eye under natural light.

As can be seen in FIG. 2, banknotes are conveyed past the head on a conveyor 10.

The two photodiodes 6 generate signals corresponding to the intensity of the incident light and these signals are fed to a microprocessor 11 where they are averaged to produce the average intensity which is used in further processing to obtain a measure of the diffuse reflectivity of the banknote. This processing takes into account the intensity signal generated by the photodiodes when no banknote 3 is present. In this case, light will impinge directly on the white surface of a hard impervious member (or tile) 8 placed close behind the nominal plane of the banknote. This surface is visible to the detector head between banknotes, and is used to standardise the output of the detector, and to compensate for dust build up on the windows of the head.

Figure 3:
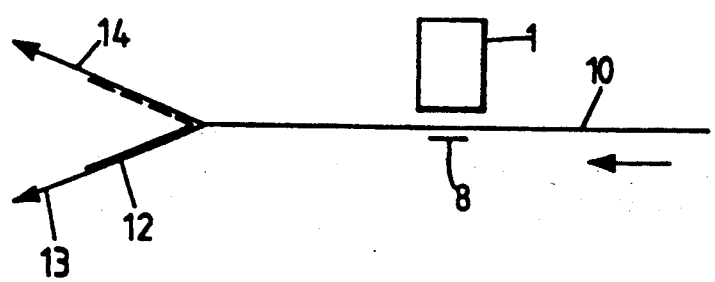
FIG. 3 illustrates schematically part of a banknote feed system incorporating the detector of FIG. 1.

The microcomputer 11 determines the diffuse reflectivity at a series of positions along the banknote and then performs on the determined reflectivities one or more algorithms to determine whether the banknote is acceptable or not. A signal representing this determination is fed to a diverter 12 downstream of the detector which causes the banknote to be fed to a dump along a path 13 if the banknote is unacceptable or towards further detection apparatus or an output station along a path 14 if the banknote is acceptable as indicated by a dashed line in FIG. 3.

Figure 5:
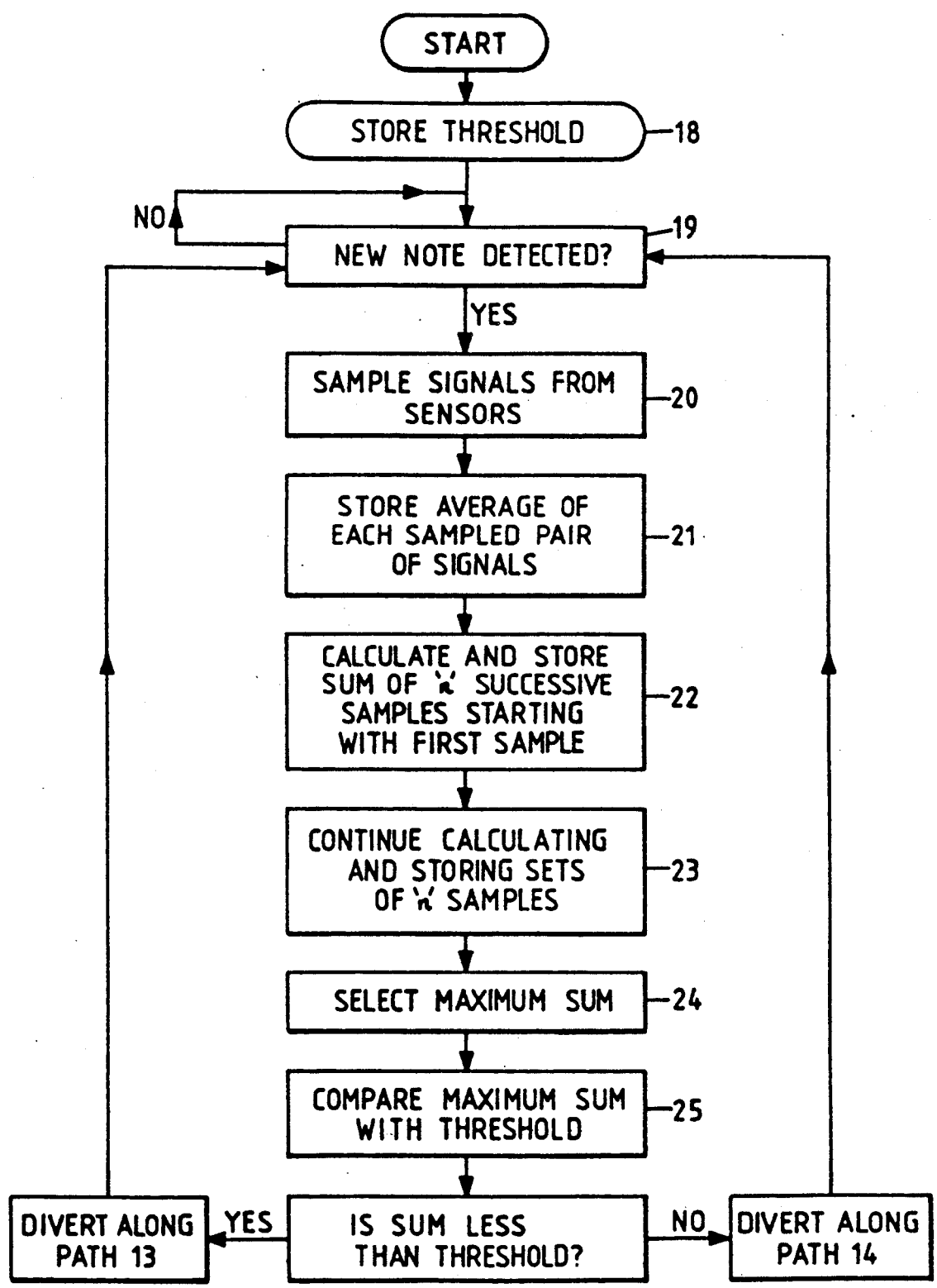
FIG. 5 is a flow diagram illustrating operation of the apparatus.

In operation (FIG. 5) the microprocessor 11 initially stores a threshold (step 18) for the banknotes to be fed. The apparatus then monitors for the arrival of a banknote by sensing the output of the photodiodes 6 (step 19). When a note is sensed, the outputs from the photodiodes 6 are regularly sampled (step 20), averaged and stored (step 21) in a memory of the microprocessor 11. A soil detection algorithm is then carried out. This algorithm assumes that the reflectance signal is sampled at fixed time intervals which represent fixed increments of distance along the document.

The value of "n" is chosen at the time the system is configured for a particular document. A degree of control over the threshold value may be provided.

The algorithm selects the lightest extended region of the document as being the most representative of the soiled state of the document, so as to match the type of analysis used by a human observer and also to minimise the effects of variation in the density of printing inks. The algorithm is as follows.

1. Calculate and store the sum of "n" successive samples, starting with the first sample of the document (step 22).
2. Repeat step 1 for sums starting with the second sample, third, fourth sample, etc.
3. Continue calculating the sums until the last sample of the document is included in a sum (step 23).
4. Select the maximum sum value as being the measure of the soiled state of the document (step 24).
5. Compare the maximum sum with the threshold value representing the borderline between fit and unfit documents to decide whether a sampled document is fit or unfit (step 25).

If the maximum sum is less than the threshold this indicates an unfit note which is passed along path 13 to the dump. Otherwise the note is passed along path 14 by suitably actuating the diverter 12.

Figure 4A:
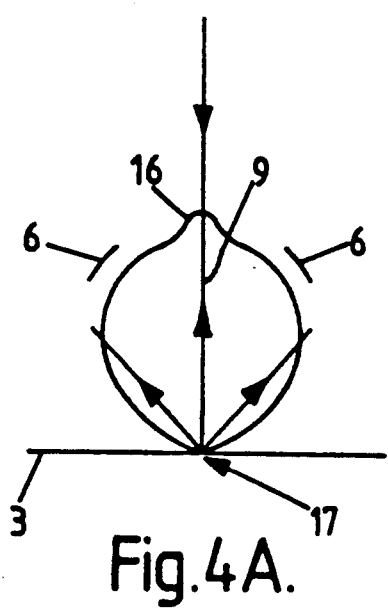
FIGS. 4A and 4B are polar diagrams illustrating the variation in intensity of reflected light with reflectance angle for two different angles of incidence.

The reason for positioning the photodiodes 6 and windows 7 in the locations shown in FIG. 1 can be seen in FIG. 4A. This shows the variation in intensity of reflected light with direction in accordance with the Lambertian Law. In this case, the direction of the incident light 9 is normal to the banknote 3. There is a very high reflected intensity in line with this as indicated at 16 and this corresponds to the specularly reflected light. It will be noticed that the variation in intensity of the remaining diffusely reflected light is generally symmetrical about the position 17 of the banknote 3 which is illuminated and about the region through which the specularly reflected radiation passes. The photodiodes 6 are positioned therefore at corresponding positions on each side of the line of symmetry. If the angle of incidence should change due for example to a crinkle or fold in the banknote 3 this will be equivalent to rotation of the banknote 3 about the point of illumination 17 resulting in rotation of the polar diagram. It is clear from this diagram that such a rotation will result in an increase in the intensity of diffuse radiation received by one sensor and a corresponding reduction at the other sensor. The average of the two sensors, will remain the same providing the degree of rotation is not such that significant specularly reflected light is received by one of the sensors.

Figure 4B:
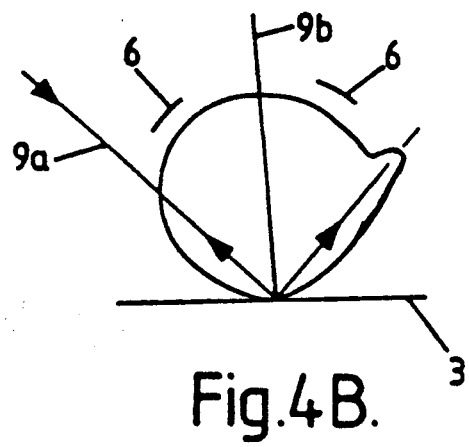

FIG. 4B illustrates another example in which the angle of illumination is indicated by an arrow $9a$. For the same reasons, the sensors 6 are positioned at corresponding positions on either side of the line of symmetry $9b$.

Figure 6:
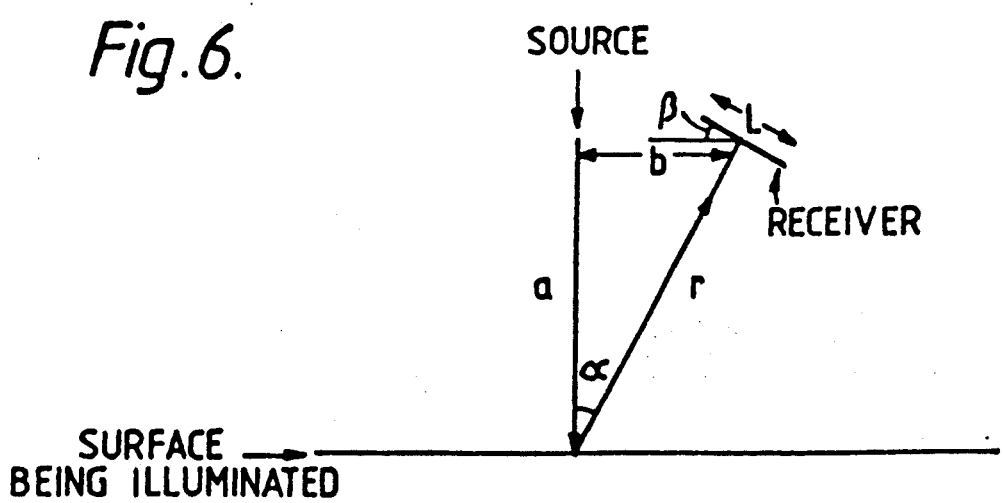
FIG. 6 is a diagram indicating the geometry of illuminating and receiving radiation from a surface.

The geometry of illuminating and receiving radiation from a surface is shown in FIG. 6. The distances and angles need no explanation beyond confirming that "a" is the perpendicular distance between the centre of the sensing position (sensor) and the surface under examination, and that "b" is the perpendicular displacement between the beam of radiation from the point of illumination (source) and the centre of the sensing position.

If the intensity of the surface illumination is arranged to be constant with variations of "a" (commonly achieved by collimation or focusing of the illumination) then the strength of the signal will be proportional to the following terms:

$\cos \alpha$ - Lambertian distribution of the reflected light.
$1r^2$ - inverse square law.
$L.\cos(\alpha-\beta)$ - area of detector normal to incident light.

As L will be constant for any one detector, the total signal will be proportional to $$(1r^2)\cos \alpha . \cos(\alpha-\beta)$$

By geometry and trigonometry this becomes $$(1/r^2)\cos\alpha(\cos\alpha\cos\beta + \sin\alpha\sin\beta) =$$

$$(1/r^2)\frac{a}{\sqrt{a^2+b^2}}\left(\frac{a}{\sqrt{a^2+b^2}}\cos\beta + \frac{b}{\sqrt{a^2+b^2}}\sin\beta\right) =$$

$$(1/r^2)\frac{a}{(a^2+b^2)}(a\cos\beta + b\sin\beta) =$$

$$\frac{a}{(a^2+b^2)^2}(a\cos\beta + b\sin\beta)$$

In the limiting case when $\beta=0°$, this reduces to $$\frac{a^2}{(a^2+b^2)^2}$$

Figure 7:
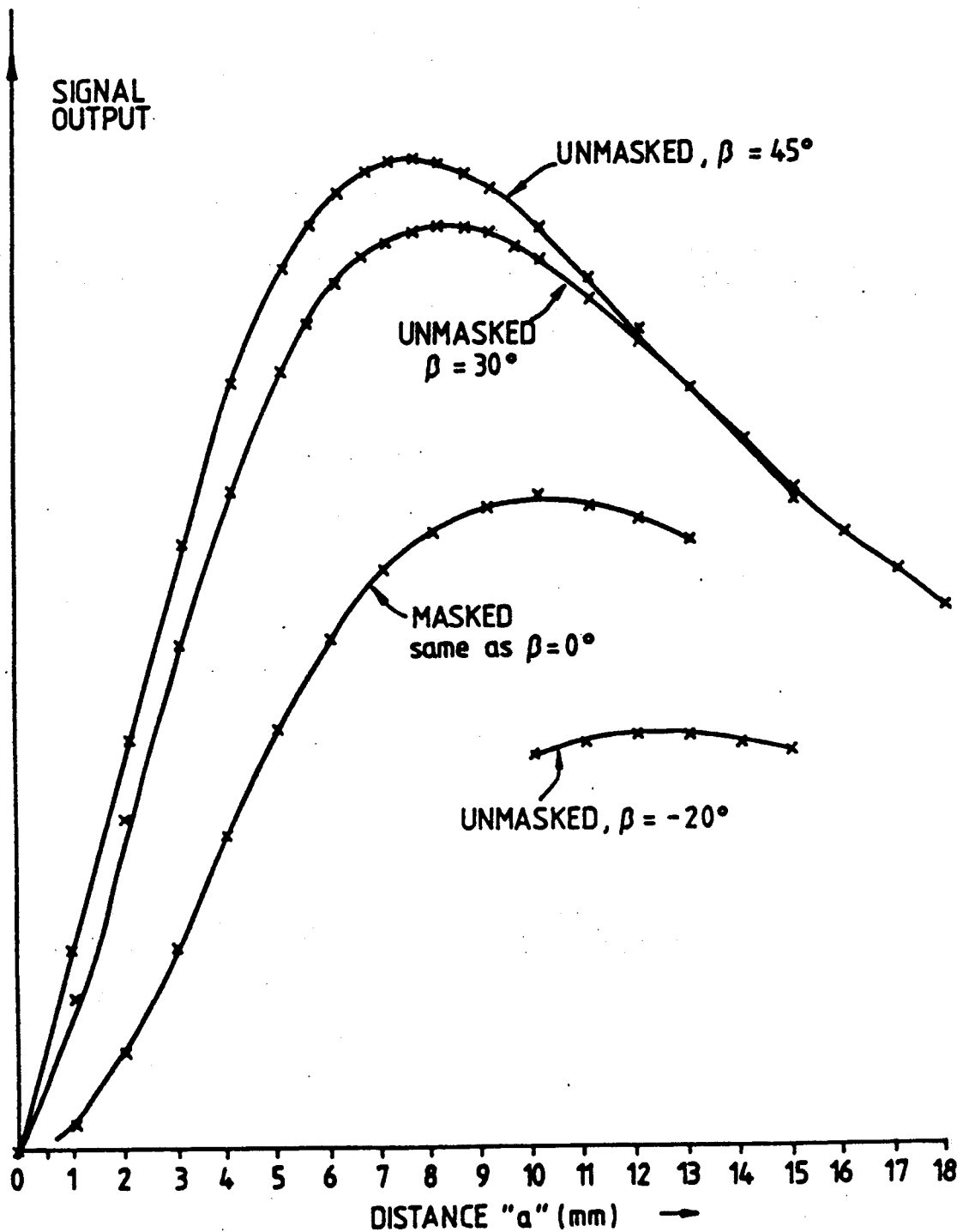
FIG. 7 is a graph showing a family of curves showing the variation of the amount of the sensed diffusely reflected radiation with the perpendicular working distance of the sensing position from the surface under examination.

A family of curves derived from this equation is shown in FIG. 7. Each of the curves uses a value for "b" of 10 mm and clearly shows a maximum at which the percentage variation of signal strength with variation of working distance is at a minimum. The curves become flatter as "$\beta$" is reduced, as shown, from 45° through 30° and 0° to −20°. All of the curves are for an unmasked sensor at the sensing position, apart from one in which the presence of the mask has given an effective value for "$\beta$" of 0°. In other words, the apertured mask is parallel to the surface under examination.

Figure 8:
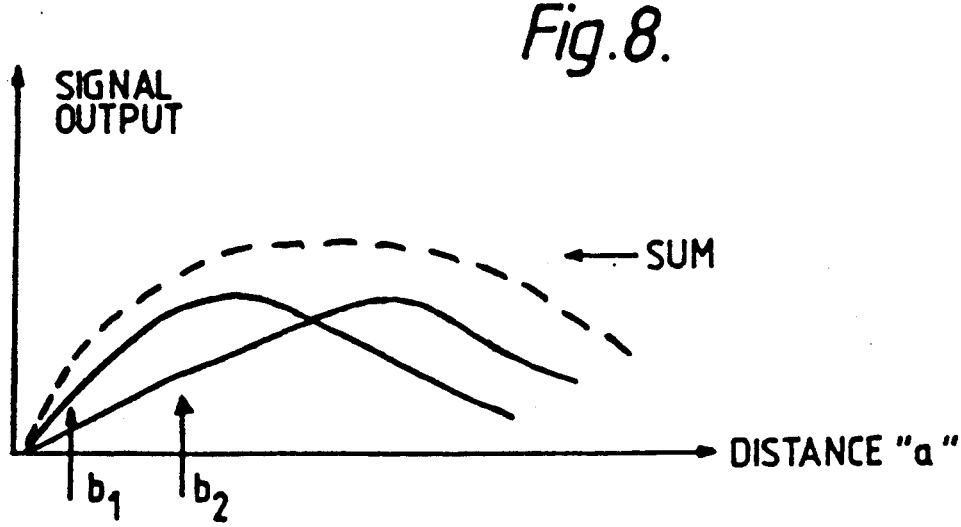
FIG. 8 is a sketch indicating the effect of a non-symmetrical arrangement of two sensing positions.

If two sensing positions are provided, and their displacements "b" are made slightly different from one another, then two separate curves for $b_1$ and $b_2$ are obtained which are displaced from one another as shown in FIG. 8. The sum of the two curves is then flatter than either of the constituent curves over an extended range of the working distances, although this does degrade somewhat the compensation for angular effects. In a similar manner, the two sensing positions could have different values for "a".

Thus, in embodying the teachings of the present invention in the above described example, the nominal working distance D between the housing 1 and the support 10 is set to correspond to a position at the centre of the plateau region of the curve for the chosen values of "b" and "$\beta$". Thereafter, variations in the distance D during the feeding of the banknote 3 past the housing 1 will result in little change in the radiation received at each window 7. The windows 7 may be rectangular, and the illuminated area may be 10 mm by 2.5 mm. In typical examples, the or each of the sensing positions is situated at an angle of between +20° and −20° relatively to the surface 3, and/or at a separation distance "b" of between 10 mm and 17 mm perpendicularly to the beam of radiation 9 before diffuse reflection by the surface 3, for a working range of distances D of between 8 mm and 15 mm perpendicularly to the surface 3.

We claim:

1. A method of monitoring the diffuse reflectivity of a portion of a surface (3), the method comprising:
   exposing the surface portion to a beam of radiation (9);
   sensing the intensity of a part of the diffuse radiation, reflected by the surface portion, at two sensing positions situated such that the intensity of the diffusely reflected radiation, sensed at each sensing position, is substantially invariant within a working range of distances (D) between the sensing position and the surface portion, the size and position of the surface portion within the plane of the surface being substantially constant within the working range of distances; and
   determining from each sensed intensity a value representative of the diffuse reflectivity of the surface portion;
   the method further comprising:
   arranging the sensing positions in symmetrical locations to either side of the beam of radiation; and
   averaging the intensities sensed at the sensing positions to obtain a diffuse reflectivity value for the surface portion which is substantially invariant to folds and creases in the surface portion.

2. A method according to claim 1, further comprising placing respective apertured masks between two radiation sensors (6) and the surface portion such that an aperture (7) in each apertured mask is situated at a respective sensing position and is co-planar with the other aperture in the other apertured mask.

3. A method according to claim 1, comprising filtering the light which reaches each sensing position to match the response of the system, substantially to the response of the human eye.

4. A method according to claim 1, comprising carrying out the steps of the method on successive portions of the surface.

5. A method according to claim 4, comprising storing the values obtained from successive portions of the surface; summing n successive values, starting with the first value; repeating the summing step for sets of n values starting with the second, third, fourth, etc value, until the last value obtained from the surface is included in a sum; and comparing the maximum of the sums with a threshold value to ascertain whether the soil state of the surface is acceptable or unacceptable.

6. A method according to claim 1, wherein the beam of radiation (9) comprises white light.

7. A method according to claim 1, comprising causing a reference surface (8) to be exposed to the beam of radiation (9), sensing diffuse radiation reflected by the reference surface at each sensing position to generate respective reference values, and subsequently normalising the intensities sensed at each sensing positions by comparison with the respective reference values.

8. A method according to claim 1, wherein the surface (3) is defined by a sheet, the method further comprising causing the sheet to move in one of two directions (13, 14) according to the diffuse reflectivity of a portion of the surface.

9. Apparatus for monitoring the diffuse reflectivity of a surface, the apparatus comprising:
   a radiation beam source (2);
   a surface support member (10) mounted such that the radiation impinges, in use, on a surface (3) supported by the support member such that the size and position of a portion of the surface within the plane of the surface and exposed to the radiation beam remains substantially constant with variations within a working range of separations between the surface and the support member; and
   two radiation sensors (6) for generating respective signals for feeding to processing means (11); each signal corresponding to the intensity of a part of the diffuse radiation reflected by the surface and passing through a sensing position, and each sensing position being situated such that the intensity of the diffusely reflected radiation sensed thereat is substantially invariant within a working range of distances (D) between the sensing position and the surface portion (3);

the sensing positions being arranged in symmetrical locations to either side of the beam of radiation;

the apparatus further comprising means for averaging the respective signals sensed at the sensing positions to obtain a diffuse reflectivity value for the surface portion which is substantially invariant to folds and creases in the surface portion.

10. Apparatus according to claim 9, wherein respective apertured masks are placed between two radiation sensors (6) and the surface (3) such that an aperture (7) in each apertured mask is situated at a respective sensing position and is co-planar with the other aperture in the other apertured mask.

11. Apparatus according to claim 1, wherein there is a filter for each sensing position to match the response of the system substantially to the response of the human eye.

12. Apparatus according to claim 9, wherein the source includes focussing means (4) to focus the beam of radiation (9) on a surface supported by the support member (10) in use.

13. Apparatus according to claim 90, wherein at least part of the support member (10) is movable relatively to the beam of radiation (9) and each sensing position whereby a series of positions on the surface is scanned.

14. Apparatus according to claim 9, wherein a reference surface (8), which is illuminated when no surface (3) is supported, has a substantially uniform reflectance whereby radiation received at each sensing position, after reflection by said uniform reflectance part (8), is used to set a reference.

15. Apparatus according to claim 14, wherein the part (8) of the support member (10) having a uniform reflectance reflects white light.

16. Apparatus according to claim 9, wherein each sensing position is situated at an angle of between +20° and −20° relatively to the surface (3), and/or at a separation of between 10 mm and 17 mm perpendicularly to the beam of radiation (9) before diffuse reflection by the surface (3), for a working range of distances (D) of between 8 mm and 15 mm perpendicularly to the surface (3).

17. Apparatus according to claim 9, further comprising transport means (10) for conveying single sheets (3) past the region which is irradiated; processing means (11) connected to each sensor (6) for determining the diffuse reflectivity of the surface and for determining the acceptability of each sheet (3); and a diverter (12) controlled by said processing means (11) to divert each sheet (3) in one of two directions according to whether the sheet is determined to be acceptable or unacceptable.

* * * * *